US012694973B2

(12) United States Patent (10) Patent No.: US 12,694,973 B2
Scherrer et al. (45) Date of Patent: Jul. 28, 2026

(54) SMART RADIOLOGY IMAGING APPOINTMENT SCHEDULING

(71) Applicant: QUANTIVLY INC., Somerville, MA (US)

(72) Inventors: Benoit Scherrer, Somerville, MA (US); Robert D. MacDougall, La Mesa, CA (US); Dimitri Falco, Dexter, MI (US)

(73) Assignee: QUANTIVLY INC., Somerville, MA (US)

( * ) Notice: Subject to any disclaimer, the term of this patent is extended or adjusted under 35 U.S.C. 154(b) by 355 days.

(21) Appl. No.: 18/452,317

(22) Filed: Aug. 18, 2023

(65) Prior Publication Data

US 2024/0062886 A1 Feb. 22, 2024

Related U.S. Application Data

(60) Provisional application No. 63/399,364, filed on Aug. 19, 2022.

(30) Foreign Application Priority Data

Aug. 18, 2022 (FR) ...................................... 2208382

(51) Int. Cl.
*G16H 40/20* (2018.01)
(52) U.S. Cl.
CPC .................................. *G16H 40/20* (2018.01)
(58) Field of Classification Search
CPC .............................. G16H 40/20; G16H 30/20
See application file for complete search history.

(56) References Cited

U.S. PATENT DOCUMENTS 6,603,494 B1 8/2003 Banks
6,988,074 B2 1/2006 Koritzinsky
(Continued)

FOREIGN PATENT DOCUMENTS

DE 10126571 1/2002
DE 102012212265 A1 1/2014
(Continued)

OTHER PUBLICATIONS

International Search Report and Written Opinion issued in App. No. PCT/US2023/072464, mailing date Nov. 28, 2023, 9 pages.
(Continued)

*Primary Examiner* — Chinyere Mpamugo
(74) *Attorney, Agent, or Firm* — Blueshift IP; Robert Plotkin

(57) ABSTRACT

A computer-implemented method and system train a model of imaging examinations based on data representing a plurality of historical imaging examinations, and generate, using the model of imaging examinations and a current schedule of imaging appointments, a schedule recommendation. The schedule recommendation recommends an imaging appointment within the current schedule of imaging appointments. The current schedule of imaging appointments may be updated based on the schedule recommendation, such as by adding the recommended imaging appointment to the current schedule or by modifying an existing imaging appointment in the current schedule. The schedule recommendation may be generated in response to a request or dynamically.

20 Claims, 3 Drawing Sheets

(56) References Cited

U.S. PATENT DOCUMENTS

| | | | |
|---|---|---|---|
| 7,542,792 | B2 | 6/2009 | Wollenweber |
| 7,676,463 | B2 | 3/2010 | Thompson |
| 7,685,262 | B2 | 3/2010 | Choubey |
| 7,885,828 | B2 | 2/2011 | Glaser-Seidnitzer |
| 8,010,382 | B2 | 8/2011 | Chua |
| 8,175,892 | B2 | 5/2012 | Kapoor |
| 8,452,615 | B2 | 5/2013 | Abri |
| 8,705,819 | B2 | 4/2014 | Carlsen |
| 9,262,514 | B2 | 2/2016 | Eckardt, III |
| 9,317,580 | B2 | 4/2016 | Cohen-Solal |
| 10,049,301 | B2 | 8/2018 | Kluckner |
| 10,324,594 | B2 | 6/2019 | Meyer |
| 10,346,586 | B2 | 7/2019 | Seethamraju |
| 10,470,739 | B2 | 11/2019 | Raman |
| 10,600,136 | B2 | 3/2020 | Cohen-Solal |
| 10,709,407 | B2 | 7/2020 | Stevens |
| 10,997,530 | B2 | 5/2021 | Bollapragada |
| 2006/0143044 | A1 | 6/2006 | Conry |
| 2006/0143060 | A1 | 6/2006 | Conry |
| 2006/0269167 | A1 | 11/2006 | Venkatesan |
| 2007/0282476 | A1 | 12/2007 | Song |
| 2008/0119717 | A1 | 5/2008 | Profio |
| 2009/0164236 | A1 | 6/2009 | Gounares |
| 2013/0090946 | A1 | 4/2013 | Foo |
| 2014/0221832 | A1 | 8/2014 | El-Zehiry |
| 2014/0379410 | A1 | 12/2014 | Lee |
| 2015/0081315 | A1 | 3/2015 | Baker |
| 2015/0081326 | A1 | 3/2015 | Krishnapuram |
| 2015/0317441 | A1 | 11/2015 | Lorman |
| 2016/0012182 | A1 | 1/2016 | Golay |
| 2017/0185713 | A1 | 6/2017 | Bhatia |
| 2018/0254098 | A1 | 9/2018 | Allmendinger |
| 2018/0294056 | A1 | 10/2018 | Rothgang |
| 2019/0074083 | A1 | 3/2019 | Jung |
| 2020/0020098 | A1 | 1/2020 | Odry |
| 2020/0043616 | A1 | 2/2020 | Saalbach |
| 2020/0092465 | A1* | 3/2020 | Lee ..................... H04N 23/675 |
| 2020/0097767 | A1 | 3/2020 | Perry |
| 2021/0023394 | A1 | 1/2021 | Da Silva Rodrigues |
| 2021/0027883 | A1* | 1/2021 | Kumar .................. G16H 40/20 |
| 2021/0035296 | A1 | 2/2021 | Mahrooghy |
| 2021/0050092 | A1 | 2/2021 | Schirra |
| 2021/0059631 | A1 | 3/2021 | Lewis |
| 2021/0118554 | A1 | 4/2021 | Amthor |
| 2021/0193331 | A1 | 6/2021 | Raman |
| 2021/0295984 | A1 | 9/2021 | Prokle |
| 2021/0295985 | A1 | 9/2021 | Prokle |
| 2021/0365815 | A1 | 11/2021 | Bonutti |
| 2022/0004960 | A1 | 1/2022 | Yang |
| 2023/0222771 | A1 | 7/2023 | Beaumont |
| 2023/0317219 | A1* | 10/2023 | Lewis .................... G16H 10/60 705/3 |
| 2023/0360778 | A1* | 11/2023 | Cochran ................ G06Q 10/10 |

FOREIGN PATENT DOCUMENTS

| | | | |
|---|---|---|---|
| DE | 102017203315 | A1 | 9/2018 |
| EP | 3696819 | A1 | 8/2020 |
| JP | 6747804 | | 8/2020 |
| JP | 2022023836 | | 2/2022 |
| KR | 20150002284 | | 1/2015 |
| KR | 20160110252 | | 9/2016 |
| KR | 20190109141 | | 9/2019 |
| KR | 20200041813 | | 4/2020 |
| KR | 20210115318 | | 9/2021 |
| WO | 9725682 | | 7/1997 |
| WO | 2017151759 | A1 | 9/2017 |
| WO | 2019040534 | A1 | 2/2019 |
| WO | 2020016451 | A1 | 1/2020 |
| WO | 2021108398 | | 6/2021 |
| WO | 2021198044 | A1 | 10/2021 |

OTHER PUBLICATIONS

International Search Report and Written Opinion issued in App. No. PCT/US2023/020807, mailing date Aug. 28, 2023, 10 pages.

Office Action (Non-Final Rejection) dated Mar. 4, 2026 for U.S. Appl. No. 18/142,820 (pp. 1-20).

2018D Edition of DICOM. PS3.3. https://dicom.nema.org/medical/dicom/2018d/output/chtml/part03/chapter_A.html (Year 2018), 24 pages.

Gauriau R, Bridge C, Chen L, Kitamura F, Tenenholtz NA, Kirsch JE, Andriole KP, Michalski MH, Bizzo BC. Using DICOM Metadata for Radiological Image Series Categorization: a Feasibility Study on Large Clinical Brain MRI Datasets. J Digit Imaging. Jun. 2020;33(3):747-762. (Year: 2020).

Manojlovi'c, T.; Stajduhar, I. Deep Semi-Supervised Algorithm for Learning Cluster-Oriented Representations of Medical Images Using Partially Observable DICOM Tags and Images. Diagnostics 2021, 11, 1920. https://doi.org/10.3390/diagnostics11101920 (Year: 2021).

Office Action (Non-Final Rejection) dated Sep. 24, 2025 for U.S. Appl. No. 18/142,820 (pp. 1-25).

Safaei. Text-based multi-dimensional medical images retrieval according to the features-usage correlation. Med Biol Eng Comput 59, 1993-2017 (2021). https://doi.org/10.1007/s11517-021-02392-0 (Year: 2021).

Extended European Search Report issued in App. No. EP23799972 dated Mar. 23, 2026 (pp. 1-13).

Communication pursuant to Rules 70(2) and 70a(2) EPC issued in App. No. EP 23799972, dated Apr. 13, 2026, 1 page.

* cited by examiner

200

START

TRAIN A MODEL OF IMAGING EXAMINATIONS BASED ON HISTORICAL IMAGING EXAMINATION DATA — 202

GENERATE A SCHEDULE RECOMMENDATION BASED ON THE MODEL OF IMAGING EXAMINATIONS ANd A CURRENT SCHEDULE OF IMAGING EXAMINATIONS — 204

UPDATE THE CURRENT SCHEDULE OF IMAGING EXAMINATIONS BASED ON THE SCHEDULE RECOMMENDATION — 206

END

SMART RADIOLOGY IMAGING APPOINTMENT SCHEDULING

CROSS-REFERENCE TO RELATED APPLICATIONS

This application claims priority to FR2208382 filed Aug. 18, 2022 and U.S. Provisional Patent Application No. 63/399,364 filed Aug. 19, 2022, titled "DIGITAL TWIN OF THE RADIOLOGY DEPARTMENT AND SMART SCHEDULING," which are incorporated by reference in its entirety.

This application is related to U.S. patent application Ser. No. 18/142,820, filed on May 3, 2023, entitled, "Identifying Medical Imaging Protocols Based on Radiology Data and Metadata," which is hereby incorporated by reference herein.

STATEMENT AS TO FEDERALLY SPONSORED RESEARCH

This invention was made with Government support under National Science Foundation (NSF) Grant No. 2036377, awarded to Quantivly, Inc., entitled, "Unified data description layer for magnetic resonance imaging scanners," and NSF Grant No. 230514, awarded to Quantivly, Inc., entitled, "Building the digital twin of radiology operations." The Government has certain rights in the invention.

BACKGROUND

Medical scanners (such as magnetic resonance imaging (MRI), computed tomography (CT), and X-ray scanners) are scarce and expensive resources. For these and other reasons, it is highly desirable to utilize medical scanners as efficiently as possible. Unfortunately, suboptimal scheduling of patients is a major cause of suboptimal medical scanner utilization. Although improving patient scheduling would increase the utilization of medical scanners, such scheduling is a difficult problem for many reasons.

For example, scheduling involves finding a solution to a problem with many requirements and constraints among many requirements and constraints, such as the current schedule, exam requirements, patient requirements, scanner capabilities, and the patient's preferred location. Optimizing for such variables simultaneously is challenging. For example, the best choice of scanner for an examination depends on the characteristics of the patient to be scanned, the clinical indication for the patient, and the corresponding imaging protocol to be used. The best choice of staff for an examination depends on the scanner protocol, the scanner, and the clinical indication. The best choice of day and time for an examination depends on the staff, scanner availability, the patient, and the other examinations that have already been scheduled. The best choice of slot duration depends on the expected duration of the protocol to image on a given scanner, on the characteristics of the patient to be scanned and its clinical indication. The best choice of inter-exam time depends on the characteristics of the patient and its clinical indication as well. As this short list of considerations makes evident, reconciling all of these considerations can be complicated. Today scanners typically are scheduled manually by operators who do not have medical training which makes reconciling all these considerations even more complicated. These operators are unable to consistently generate schedules that result in high scanner utilization and scheduling mistakes are common.

Furthermore, most radiology departments and imaging centers use a single slot duration (such as 40 minutes) for all examinations, regardless of the type of examination being performed. If the amount of time required for the examination (e.g., 60 minutes) is greater than the standard slot duration, then typically two slots (e.g., two back-to-back 40-minute slots), each having the standard slot duration, are scheduled. Similarly, if the amount of time required for the examination (e.g., 15 minutes) is less than the standard slot duration, then typically a single slot of the standard slot duration is scheduled. As can be seen from these examples, this results in more time being reserved than is required for examinations because of the inability to tailor the amount of time scheduled to the needs of each examination. Although some centers use a small number of slot sizes (e.g., 30 minutes, 45 minutes, 60 minutes, and 75 minutes), this makes the scheduling task more complicated and often leads to additional mistakes and inefficiencies. Some centers want to satisfy patients' preferred scan times as much as possible, e.g., by offering all available slots by increments of 10 minutes; most often leading to "holes" in the schedule that are too small in which to complete any other imaging examinations.

In addition, when using existing scheduling techniques, last minute scheduling (such as in the case of emergencies and patients who fail to show up for their scheduled examination) is highly disruptive to existing scanner schedules and leads to additional inefficiencies. Such exceptions typically are handled by operators who make their best efforts to rearrange the existing schedule manually, typically requiring urgent phone calls to scanner operators.

In all of the cases described above, the specific needs and characteristics of the patient, and the specific features of available scanners, often are not taken into account when scheduling examinations. This often results in scheduling slots which are too short or too long for the needs of the patient, and in mismatches between the patient's needs and the scanner's capabilities.

Attempts to address the scheduling problem using classical methodologies (e.g., Lean and Six Sigma) have faced significant limitations, such as the significant amount of time (and corresponding cost) required to gather data, the fact that data are gathered at only one point (or a very limited number of points) in time, and the hidden costs resulting from ignoring second-order, unintended consequences, which typically are not identified until post-implementation.

Furthermore, because existing scheduling relies so heavily on the knowledge and skill of human operators, where such knowledge and skill has been gained through experience and has not been systematized or recorded, the ability to transfer such knowledge and skill to other operators is limited, time-consuming, costly, and prone to error. As a result, training new operators is slow and costly, resulting in particularly suboptimal scanner scheduling and poor matches between patients and scanners while new operators are being trained.

What is needed, therefore, are improved techniques for augmenting (or replacing) scheduling operators, increasing the utilization of medical scanners, and increasing access to medical imaging for patients while providing personalized imaging procedures more tailored to individuals' needs.

SUMMARY

A computer-implemented method and system train a model of imaging examinations based on data representing a plurality of historical imaging examinations, and generate, using the model of imaging examinations and a current schedule of imaging appointments, a schedule recommendation. The schedule recommendation recommends an imaging appointment within the current schedule of imaging appointments. The current schedule of imaging appointments may be updated based on the schedule recommendation, such as by adding the recommended imaging appointment to the current schedule or by modifying an existing imaging appointment in the current schedule. The schedule recommendation may be generated in response to a request or dynamically.

Other features and advantages of various aspects and embodiments of the present invention will become apparent from the following description and from the claims.

DETAILED DESCRIPTION

A computer-implemented method and system train a model of imaging examinations based on data representing a plurality of historical imaging examinations, and generate, using the model of imaging examinations and a current schedule of imaging appointments, a schedule recommendation. The schedule recommendation recommends an imaging appointment within the current schedule of imaging appointments. The current schedule of imaging appointments may be updated based on the schedule recommendation, such as by adding the recommended imaging appointment to the current schedule or by modifying an existing imaging appointment in the current schedule. The schedule recommendation may be generated in response to a request or dynamically.

Embodiments of the present invention may be used to increase the utilization of medical scanners, especially by improving the scheduling of medical scanners for use in examinations of patients. For example, embodiments of the present invention aim to image each patient on the right scanner, at the right time, with the right slot duration, with the right staff, for the right clinical indication, while maximizing (or at least increasing) scanner utilization.

Figure 1:
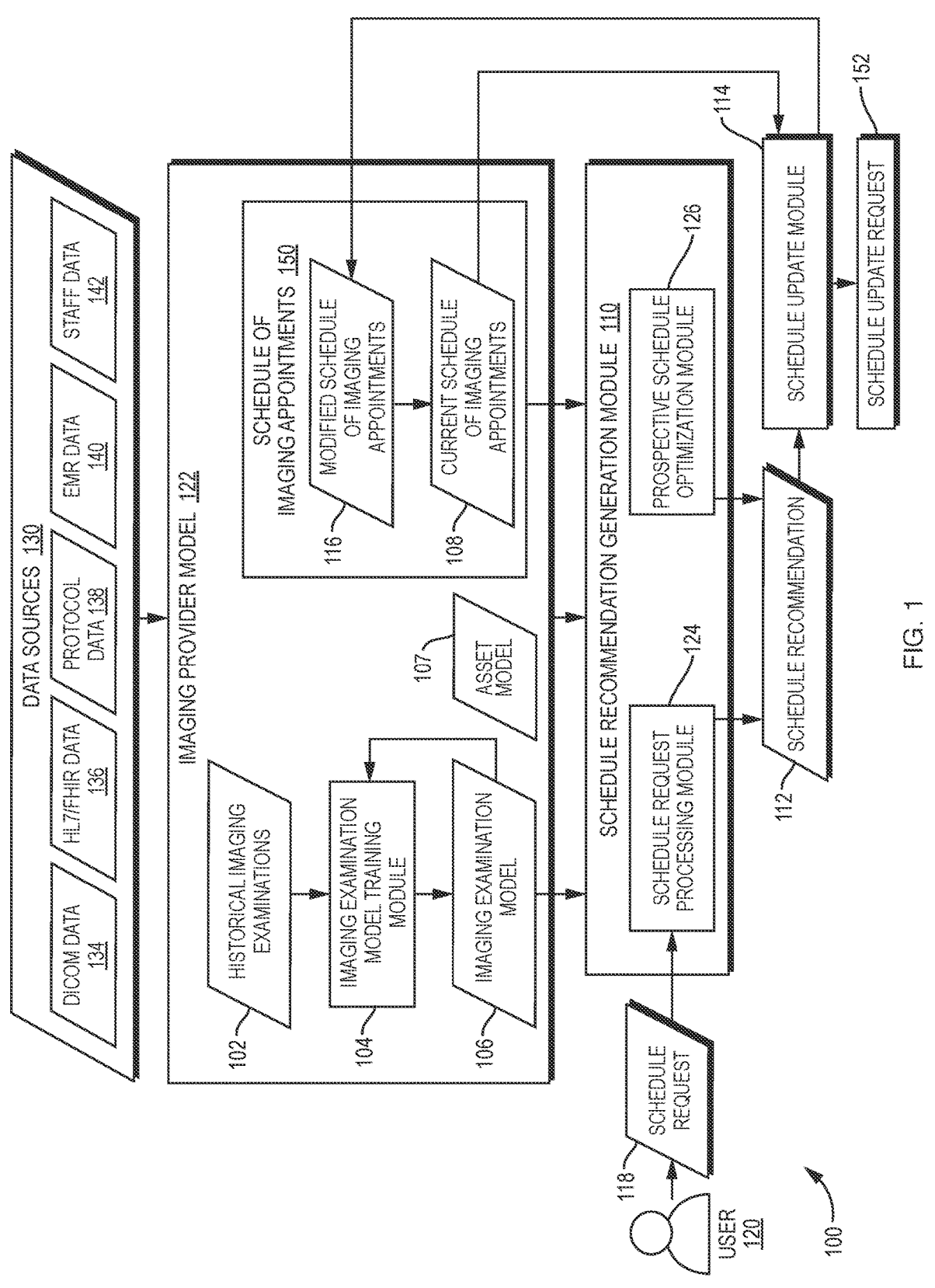
FIG. 1 is a dataflow diagram of a system for generating a schedule recommendation for an imaging appointment according to one embodiment of the present invention.
Figure 2:
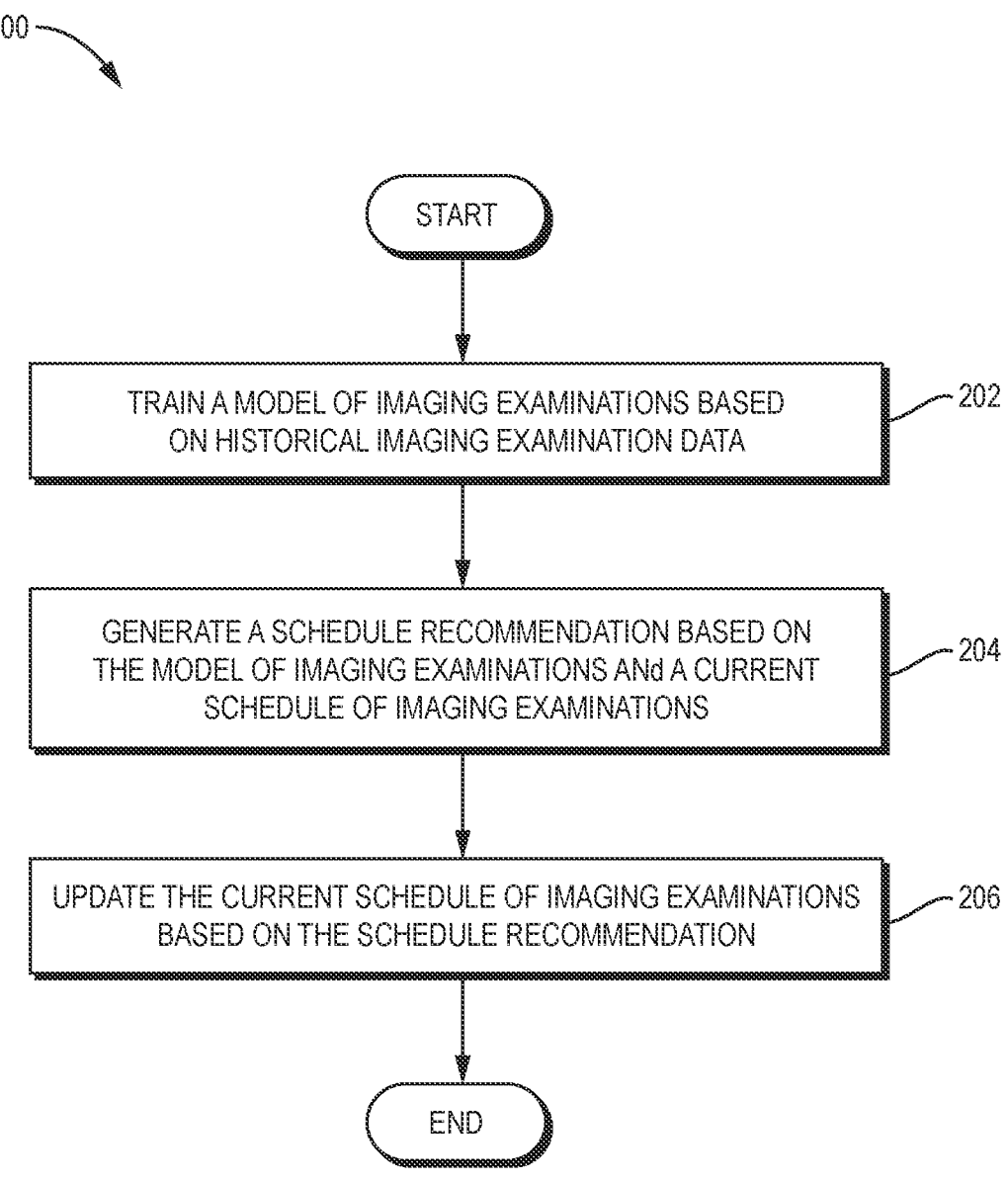
FIG. 2 is a flowchart of a method performed by the system of FIG. 1 according to one embodiment of the present invention.

Referring to FIG. 1, a dataflow diagram is shown of a system 100 for generating a schedule recommendation for an imaging appointment according to one embodiment of the present invention. Referring to FIG. 2, a flowchart is shown of a method 200 performed by the system 100 of FIG. 1 according to one embodiment of the present invention.

The system 100 includes an imaging provider model 122, which is a computerized model that synthetizes and assimilates data from various sources within an imaging provider. The term "imaging provider," as used herein, refers to one or more physical spaces, which include one or more medical scanners of any type, in any combination. An imaging provider may also include one or more patients and/or one or more staff. An imaging provider is not limited in size or configuration and may, for example, include one or more rooms, on one or more floors, in one or more buildings. An imaging provider may, for example, include one or more imaging facilities.

The imaging provider model 122 may provide a dynamic representation of the imaging provider's current state and may also include one or more models that allow predictions of future states of the imaging provider. The particular components of the imaging provider model 122 shown in FIG. 1 are merely examples and do not constitute limitations of the present invention. For example, the imaging provider model 122 may not include all of the components shown in FIG. 1, and may include components in addition to those shown in FIG. 1. The imaging provider model 122 may, for example, be a "digital twin" of the imaging provider (or any part thereof, such as one or more particular imaging facilities of the imaging provider), as that term is used herein.

In general, a scanner images the patient in what is referred to as an "imaging acquisition" or simply an "acquisition," which results in one or multiple images (also referred to herein as "acquisition data"). Associated with each such acquisition is a set of corresponding technical parameters, which are specific to the imaging modality (e.g., MRI or CT) that is employed during the acquisition. The values of those technical parameters (e.g., in MRI: echo time and repetition time, among others; in CT: kVp and mAs, among others) define a variety of settings and factors that affect the quality and characteristics of the final images, including which specific tissue properties are being assessed during the acquisition, ultimately leading to different views of the tissues imaged (e.g., T1-weighted, T2-weighted). During an "examination" (also referred to herein as an "imaging examination") the patient may undergo one or multiple acquisitions so that different, typically complementary, views of the tissues are assessed. The term "imaging protocol" (or simply "protocol") refers herein to a plurality of acquisition data sets that were acquired in a particular examination. The term "examination data set" refers herein to the following, which are associated with a particular examination: (1) a plurality of acquisition data sets that represent the acquisitions performed in a particular examination (i.e., the imaged protocol) corresponding to the examination data set; and (2) (optionally) one or more non-technical parameters, and their associated values, associated with the examination.

The system 100 (e.g., the imaging provider model 122) includes data representing a plurality of historical imaging examinations (also referred to herein as historical imaging examination data 102). The system 100 (e.g., the imaging provider model 122) also includes an imaging examination model training module 104, which trains a model of imaging examinations (also referred to herein as an imaging examination model 106), based on the historical imaging examination data 102 (FIG. 2, operation 202).

The historical imaging examination data 102 may, for example, include a plurality of data structures, each of which contains data relating to a corresponding historical imaging examination. Each such data structure in the historical imaging examination data 102 is referred to herein as a historical imaging examination data record. Each such historical imaging examination data record may include one or more "descriptors." As used herein, the term "descriptor" refers to data representing a value of a particular corresponding type of information. Different descriptors correspond to different types of information. Any particular historical imaging examination data record, corresponding to a particular historical imaging examination, may include one or more descriptors, such as any one or more of the following, in any combination:

a scheduled start time descriptor representing a start time that was scheduled for the corresponding historical imaging examination;

a scheduled slot duration descriptor representing a slot duration that was scheduled for the corresponding historical imaging examination;

a scheduled imaging protocol descriptor, representing an imaging protocol (also referred to herein as a "scanner protocol" or simply as a "protocol") that was scheduled to be used to perform the corresponding historical imaging examination;

a scheduled scanner descriptor representing a scanner that was scheduled to be used to perform the corresponding historical imaging examination;

a scheduled staff descriptor representing a technologist (also referred to herein as a "staffer," "staff member," or "staff") who was scheduled to perform the corresponding historical imaging examination (and, optionally, staff needed for administrating sedation or anesthesia);

a requesting physician descriptor representing a physician who requested the corresponding historical imaging examination;

an actual start time descriptor representing an actual start time of the corresponding historical imaging examination;

an actual duration descriptor representing an actual duration of the corresponding historical imaging examination;

an actual imaging protocol descriptor, representing an imaging protocol that was used to perform the corresponding historical imaging examination, optionally including the list of all acquisitions performed with all their acquisition technical parameters;

a list of all acquisitions performed during the corresponding historical imaging examination, optionally with some or all of the technical parameter used for such acquisitions, and optionally with the start time/duration of each such acquisition;

an actual scanner descriptor, representing a scanner that was used to perform the corresponding historical imaging examination, which may include, for example, any of the following data: scanner vendor, scanner model, scanner maximum gradient strength, available coils, software version, list of reconstruction software, availability of sedation unit, availability of motion mitigation capability, hours of operation, bore size, location (e.g., floor) within the imaging provider, and table height;

an actual staff descriptor, representing a staff member who performed and/or participated in to the corresponding historical imaging examination, which may include, for example, any of the following data: typical schedule, preferred location, languages spoken, scanners the staff member is trained on, types of patients the staff member is trained for, whether the staff member can administer an IV, and whether the staff member can administer sedation;

a patient descriptor, representing one or more characteristics of a patient on whom the corresponding historical imaging examination was performed, which may include, for example, any of the following data: age, weight, body-mass index, mobility issues, patient diagnosis, patient condition, disease severity index, whether the patient was sedated or not sedated, best time to image the patient, whether the patient is obese/pregnant/claustrophobic (for determining whether to prefer a wide bore scanner), whether the patient is geriatric/disabled (for determining whether to prefer a low table scanner), and a degree of scheduling flexibility (e.g., high flexibility for in-patients, low flexibility for out-patients);

a list of all image reconstructions performed during the corresponding historical imaging examination;

a radiologist report associated with the corresponding historical imaging examination;

preparation time required to prepare for the execution of the imaging protocol performed during the corresponding historical imaging examination;

the time at which contrast agent was injected, the amount of contrast injected, and/or the contrast product that was injected;

notes describing what happened during the examination (e.g., the patient had to go to the bathroom, the patient was poorly cooperative, the patient vomited).

Any duration descriptor may include data representing any one or more of the following, in any combination: an imaging time of the corresponding historical imaging examination, a non-imaging time (e.g., preparation time) of the corresponding historical imaging examination, and a total time (e.g., imaging time plus non-imaging time) of the corresponding historical imaging examination. The duration of an examination (also referred to herein as "examination duration") is the time difference between the acquisition time of the first data acquired by the scanner and that of the last data acquired by the scanner for the examination. This is effectively the actual amount of time that was taken to execute the protocol.

More generally, any of the historical imaging examination data records in the historical imaging examination data 102 may include any data defined by any version of the Digital Imaging and Communications in Medicine (DICOM) standard and/or any information defined by any version of the Health Level Seven (HL7) standards.

The system 100 may also include a plurality of data sources 130 containing corresponding data. Merely as examples, the plurality of data sources 130 may include DICOM data 134, HL7/FHIR data 136, protocol data 138 (e.g., for each scheduled appointment, the imaging protocol that is scheduled to be performed at that appointment), Electronic Medical Record (EMR) data 140, and/or staff data 142 (e.g., the staff that are assigned to each scheduled appointment), in any combination. The plurality of data sources 130 need not include all of the data sources shown in FIG. 1, and may include data sources not shown in FIG. 1. For example, the plurality of data sources 130 may include door lock data, sensor data, and camera data. The various components of the plurality of data sources 130 (e.g., the new patient examination data 132, DICOM data 134, HL7/FHIR data 136, protocol data 138, EMR data 140, and staff data 142 may be independent of each other and may be received and processed by the imaging provider model 122 independently of each other, or in any combination. The imaging provider model 122 may receive data from some of all of the plurality of data sources 130 as input, and may use such data in the performance of any of the functions disclosed herein, such as the training of the imaging examination model 106 by the imaging examination model training module 104.

The imaging examination model 106 may, for example, include one or more descriptors, such as one or more of any of the descriptors mentioned above, in any combination. As described in more detail below, at least some of the descriptors in the imaging examination model 106 may be generated by the imaging examination model training module 104 as part of the process of training the imaging examination model 106 (i.e., FIG. 2, operation 202). For example, the imaging examination model 106 may include descriptors representing breaks between examinations (i.e., periods of time during which examinations are not to be scheduled), even if such breaks are not labeled in the historical imaging examination data 102.

The imaging examination model 106 may feed back into the imaging examination model training module 104 to enable the imaging examination model training module 104 to update the training of the imaging examination model 106 and thereby improve the imaging examination model 106 over time. As merely one example, the imaging examination model training module 104 may determine that the imaging examination model 106 would benefit from more specific training and, in response to such a determination, the imaging examination model training module 104 may change which data the imaging examination model training module 104 samples from the historical imaging examination data 102 and use those changed data samples to update the training of the imaging examination model 106, and thereby address the identified weakness in the imaging examination model 106. This is merely an example of a variety of ways in which the imaging examination model 106 may feed back into the imaging examination model training module 104 and thereby enable the imaging examination model training module 104 to update the training of the imaging examination model 106.

The system 100 (e.g., the imaging provider model 122) also includes a schedule of imaging appointments 150, which may include a current schedule of imaging appointments (also referred to herein as a current schedule 108), representing imaging appointments which currently are scheduled to be performed at the imaging provider. As described below, the current schedule 108 may be modified (such as by adding one or more imaging appointments to it), thereby generating a modified schedule of imaging appointments 116. The modified schedule of imaging appointments 116 may then become the new current schedule of imaging appointments 108 and be used to perform any of the functions of the current schedule of imaging appointments 108 disclosed herein.

The imaging provider model 122 may include any of a variety of descriptors describing an imaging provider. For example, the imaging provider model 122 may include one or more operating hours descriptors representing operating hours of the imaging provider, such as one or more of the following: operating hours of one or more of the imaging provider's imaging facility building(s), operating hours of each of one or more staff of the imaging provider, operating hours of each of one or more scanners in the imaging provider, and operating hours of each of one or more sedation units in the imaging provider. Generating the schedule recommendation 112 may include generating the schedule recommendation 112 based on any of the data disclosed herein (e.g., the imaging examination model 106, the current schedule 108, and/or the schedule request 118) and the imaging provider model 122.

As one particular example, if the imaging provider model 122 includes a descriptor representing operating hours of the imaging provider, then generating the schedule recommendation 112 may include generating the schedule recommendation 112 to include data representing a recommendation that the imaging appointment occur within the operating hours of the imaging provider, based on the imaging examination model 106, the current schedule 108, and the imaging provider model 122 (and, optionally, the schedule request 118).

As another example, the imaging provider model 122 may include an asset model 107, which may include descriptors representing any number of assets (e.g., scanners) within the imaging provider. For example, the imaging provider model 122 may include an imaging protocol collection that represents a plurality of imaging protocols in the imaging provider (e.g., a plurality of imaging protocols that have been performed in the imaging provider and/or a plurality of imaging protocols that are available to be performed at the imaging provider).

The imaging protocol collection referred to above may, for example, be created from the protocol book of the imaging provider, and describe all imaging protocols of the imaging provider built by radiologists for each model of scanner within the imaging provider. Alternatively, the collection of imaging protocols may be built passively (e.g., automatically) by analyzing all imaging examinations performed within the imaging provider, such as in any of the ways disclosed in U.S. patent application Ser. No. 18/142, 820, filed on May 3, 2023, entitled, "Identifying Medical Imaging Protocols Based on Radiology Data and Metadata." If the imaging provider model 122 includes a collection of imaging protocols representing a plurality of imaging protocols that are available to be performed at the imaging provider, then generating the schedule recommendation 112 may include generating the schedule recommendation 112 to include data representing a recommendation that the imaging appointment perform one of the plurality of imaging protocols specified by the imaging provider model 122, based on the imaging examination model 106, the current schedule 108, and the imaging provider model 122 (and, optionally, the schedule request 118).

The imaging provider model 122 (e.g., the asset model 107) may include not only digital data representing physical elements of the imaging provider (such as scanners within the imaging provider, location, floor, and accessibility for each scanner), but also digital data representing non-physical elements of the imaging provider, such as one or more imaging protocols, the current schedule 108, and workflows performed within and/or capable of being performed by the imaging provider.

The imaging provider model 122 may, for example, be a digital twin of the imaging provider (e.g., of one or more of the imaging provider's imaging facilities). In general, a digital twin is a digital representation of a physical system, such as an imaging provider or one or more imaging facilities. Such a digital twin may, for example, be a dynamically evolving digital replica of the imaging provider that assimilates data from a plurality of sources to build a virtual, predictive model of what is happening at the imaging provider at all times (at least within some time period). One benefit of digital twins is that they enable simulations and/or performance optimization without the need to generate and operate physical prototypes.

The system 100 also includes a schedule recommendation generation module 110, which receives the imaging examination model 106 and the current schedule 108 as input and generates, based on the imaging examination model 106 and the current schedule 108, a schedule recommendation 112 (FIG. 2, operation 204). As will be described in more detail below, the schedule recommendation generation module 110 may, for example, generate the schedule recommendation 112 based on a schedule request 118, or by prospectively analyzing the current schedule 108 (using the prospective schedule optimization module 126) without receiving the schedule request 118.

The schedule recommendation 112 may recommend an imaging appointment within the current schedule 108. For example, the schedule recommendation 112 may include data representing such an imaging appointment. The schedule recommendation generation module 110 may, for example, use a constrained resource allocation algorithm to generate the schedule recommendation 112 by taking into account any one or more of the following, in any combination: the imaging examination model 106, the current schedule 108, any additional soft/hard constraints, the schedule request 118, and the imaging provider model 122.

The schedule recommendation 112 may, for example, include one or more descriptors, such as one or more of any of the descriptors disclosed herein, in any combination. As some particular examples, the schedule recommendation 112 may include any one or more of the following, in any combination:

a start time descriptor representing a recommended start time of the recommended imaging appointment;

a duration descriptor representing a recommended duration of the recommended imaging appointment;

a preparation descriptor representing information about preparation for the imaging protocol performed during the imaging appointment, such as required preparation time;

an imaging protocol descriptor (e.g., a protocol name identifier) representing a recommended imaging protocol to use when performing one or more imaging examinations in the recommended imaging appointment;

a scanner descriptor representing a recommended scanner to use when performing one or more imaging examinations in the recommended imaging appointment;

a staff descriptor representing a recommended staff member to perform one or more imaging examinations in the recommended imaging appointment; and a patient descriptor representing one or more characteristics of a patient on whom to perform one or more imaging examinations in the recommended imaging appointment (such as data representing one or more of an identity of the patient, a clinical condition of the patient, and demographic data of the patient).

If the schedule recommendation 112 includes more than one of the types of descriptors listed above, then the schedule recommendation 112 may propose different options for the same appointment (e.g., by including multiple values for the same descriptor type, e.g., the start time descriptor type), optionally with some preference score associated with each option.

Existing imaging appointment scheduling techniques typically use a relatively large fixed duration slot (e.g., 45 minutes) and either assign that fixed duration or a multiple of that fixed duration to every imaging appointment. This can result in significantly suboptimal schedules, due to the actual time required for an imaging appointment being either significantly shorter than or significantly longer than the scheduled duration of the imaging appointment. For example, if the slot time required for an imaging appointment is 60 minutes, this may result in 30 minutes of unutilized time because two slots of 45 minutes need to be reserved. Similarly, if the slot time required for an imaging appointment is 30 minutes, this may result in 15 minutes of unutilized time because the whole 45 minutes slot is reserved.

In contrast, although the schedule recommendation generation module 110 may apply some minimum granularity to the slot sizes of its outputs (e.g., 1 minute), the resulting outputs of the schedule recommendation generation module 110 may differ from each other by any amount (e.g., 1 minute, 2 minutes, 3 minutes, etc.), not merely by standard slot durations (e.g., 45 minutes). By using the imaging examination model 106 (e.g., to predict the examination duration), the schedule recommendation generation module 110 may attempt to generate outputs that statistically lead to high scanner utilization, while controlling the probability of delays, where the acceptable probability of delay for each imaging provider may be specified within a set of constraints.

The system 100 may include a schedule update module 114, which receives the current schedule 108 and the schedule recommendation 112 as input, and which updates the current schedule 108 based on the schedule recommendation 112, thereby generating a modified schedule of imaging appointments (also referred to herein as a modified schedule 116) (FIG. 2, operation 206). The modified schedule 116 may include any of the descriptors disclosed herein. As mentioned above, the modified schedule 116 may become the new current schedule 108. The schedule update module 114 may optionally generate and provide a schedule update request 152 to a scheduling system, e.g., via the HL7 or FHIR protocol.

The schedule update module 114 may update the current schedule 108 to generate the modified schedule 116 in any of a variety of ways. For example, updating the current schedule 108 to generate the modified schedule 116 may include adding the imaging appointment represented (e.g., recommended) by the schedule recommendation 112 to the current schedule 108, thereby generating the modified schedule 116. As another example, updating the current schedule 108 to generate the modified schedule 116 may include modifying an existing imaging appointment within the current schedule 108 based on the schedule recommendation 112, thereby generating the modified schedule 116.

The schedule recommendation 112 may, for example, be or include a scheduling order, or just a scheduling suggestion. As this implies, the system 100 may or may not update the current schedule 108 based on the schedule recommendation 112. In other words, the system 100 may or may not include the schedule update module 114, and the schedule update module 114 may or may not perform the update(s) disclosed herein. The schedule recommendation generation module 110 may, for example, provide the schedule recommendation 112 to an outside scheduling system via one or more HL7/FHIR messages. As another example, one or more humans may update the current schedule 108 manually based on the schedule recommendation 112. For example, the schedule recommendation 112 may be a human-readable message (e.g., an email message or a message displayed on a screen), which one or more humans may use to update the current schedule 108 manually.

When the schedule update module 114 does perform the update(s) disclosed herein, such updates may update the current schedule 108 based on the schedule recommendation 112 in any of a variety of ways. For example, if the schedule recommendation 112 includes a plurality of descriptors (e.g., descriptors representing a start time and a duration), the schedule update module 114 may update the current schedule 108 based on all of the plurality of descriptors, such as by generating the modified schedule 116 to include at least one imaging appointment that has all of the plurality of descriptors (e.g., descriptors of the start time and the duration from the schedule recommendation 112). Alternatively, however, the schedule update module 114 may update the current schedule 108 based on some, but not all, of the plurality of descriptors in the schedule recommendation 112. As one example, the schedule update module 114 may update the current schedule 108 based on the duration descriptor in the schedule recommendation 112, but not based on the start time descriptor in the schedule recommendation 112, such that the modified schedule 116 includes an imaging appointment having the duration specified by the schedule recommendation 112's duration descriptor, but not having the start time specified by the schedule recommendation 112's start time descriptor.

The schedule recommendation generation module 110 may generate the schedule recommendation 112 (FIG. 2, operation 204) automatically, i.e., not in response to any human input. For example, the schedule recommendation generation module 110 may include a prospective schedule optimization module 126, which may generate the schedule recommendation 112 automatically (e.g., without receiving or processing the schedule request 118) based on any one or more of the imaging examination model 106, the current schedule 108, and the imaging provider model 122. For example, the prospective schedule optimization module 126 may repeatedly (e.g., periodically or continuously), prospectively and automatically perform operation 204 to generate one or more schedule recommendations based on the state of the imaging examination model 106, the current schedule 108, and (optionally) the imaging provider model 122 at the time of performing each instance of operation 204. In this way, the prospective schedule optimization module 126 may generate schedule recommendations dynamically in response to changes in the imaging examination model 106, the current schedule 108, and (optionally) the imaging provider model 122. As one particular example, if an imaging appointment is removed (i.e., canceled) from the current schedule 108, the prospective schedule optimization module 126 may automatically generate one or more schedule recommendations, using the techniques disclosed herein and based on the updated current schedule 108 and the imaging examination model 106 (and optionally the imaging provider model 122). One or more of such generated schedule recommendations may, for example, recommend scheduling an imaging appointment during the time of the imaging appointment that was removed from the current schedule 108. As another example, if a patient checks in early, the prospective schedule optimization module 126 may move the patient to a different scanner than originally scheduled if one is available (while respecting constraints in the system 100). As another example, if an examination of a patient runs longer than scheduled, one or more other patients may be reshuffled across scanners (while respecting constraints in the system 100).

Similarly, the schedule update module 114 may update the current schedule 108 to generate the modified schedule 116 (FIG. 2, operation 204) automatically, i.e., not in response to any human input. For example, the schedule update module 114 may automatically perform operation 206 in response to receiving the schedule recommendation 112 or otherwise in response to detecting that the schedule recommendation 112 has been generated. When combined with automatic generation of schedule recommendations by the schedule recommendation generation module 110, this enables the system 100 to automatically and dynamically generate and update imaging appointments within the current schedule 108 and the modified schedule 116 to reflect changes in the imaging examination model 106, the current schedule 108, and (optionally) the imaging provider model 122.

The schedule recommendation generation module 110 may, however, include a schedule request processing module 124, which may receive a schedule request 118 from a requestor (e.g., a user 120), and generate the schedule recommendation 112 based on the imaging examination model 106, the current schedule 108, the schedule request 118, and (optionally) the imaging provider model 122. The schedule request 118 may, for example, include one or more descriptors, such as one or more of any of the descriptors disclosed herein, in any combination. As some particular examples, the schedule request 118 may include any one or more of the following, in any combination:

a patient descriptor representing one or more characteristics of a patient on whom to perform one or more imaging examinations in the requested imaging appointment (such as any of the patient descriptors disclosed herein, e.g., data representing one or more of an identity of the patient (e.g., a unique identifier of the patient), a clinical condition of the patient, and demographic data of the patient);

an imaging protocol descriptor representing a requested imaging protocol to use when performing one or more imaging examinations in the requested imaging appointment;

a scanner descriptor representing a requested scanner to use when performing one or more imaging examinations in the requested imaging appointment;

a staff descriptor representing a requested staff member to perform one or more imaging examinations in the requested imaging appointment;

a start time descriptor representing one or more preferred start times of the requested imaging appointment; and a duration descriptor representing a requested duration of the requested imaging appointment.

The schedule request processing module 124 may, for example, obtain and/or generate data based on the schedule request 118 before generating the schedule recommendation 112, and use such obtained/generated data to generate the schedule recommendation 112. For example, if the schedule request 118 includes a patient identifier but not additional information about the patient, the schedule request processing module 124 may use the patient identifier to obtain additional information about the patient (e.g., one or more clinical conditions of the patient, demographic data of the patient, and data from one or more previous imaging appointments of the patient, such as one or more imaging protocols previously used in one or more imaging examinations of the patient), such as by looking up such additional information in a data store containing such additional information (e.g., an existing data store in a hospital, or the imaging provider model 122). As this implies, the schedule request 118 may contain only a subset of the information that the schedule recommendation generation module 110 uses to generate the schedule recommendation 112, and the schedule recommendation generation module 110 may obtain and/or generate information that is missing from the schedule request 118 and use such obtained/generated information to generate the schedule recommendation 112.

As the above implies, the schedule recommendation generation module 110 may generate the schedule recommendation 112 either in response to the schedule request 118 (using the schedule request processing module 124) or by analyzing the current schedule 108 using the prospective schedule optimization module 126, without receiving the schedule request 118. As this implies, the schedule recommendation generation module 110 may generate the schedule recommendation 112 without receiving and/or processing the schedule request 118. As this also implies, in some embodiments of the present invention, the schedule recommendation generation module 110 may generate some instances of the schedule recommendation 112 using the prospective schedule optimization module 126 in the ways disclosed herein (e.g., by analyzing the current schedule 108 automatically and without receiving or processing the schedule request 118), and may generate other instances of the schedule recommendation 112 using the schedule request processing module 124 in the ways disclosed herein (e.g., by receiving and processing the schedule request 118).

The schedule recommendation 112 may include one or more descriptors that are not contained in the schedule request 118. For example, the schedule recommendation 112 may include a "duration" descriptor having a particular value (e.g., 30 minutes), even if the schedule request 118 does not include a "duration" descriptor. In such a case, the schedule recommendation generation module 110 may generate the "duration" descriptor (and its value) in the schedule recommendation 112 in any of a variety of ways. For example, the schedule recommendation generation module 110 may generate the "duration" descriptor (and its value) using the imaging examination model 106.

As another example, the schedule recommendation 112 may include a descriptor that is contained in the schedule request 118, but that descriptor may have a different value in the schedule request 118 than in the schedule recommendation 112. For example, the schedule request 118 may include a "start time" descriptor having a particular value (e.g., 2:00 PM on a particular date), and the schedule recommendation 112 may have its own "start time" descriptor with a different value than that of the schedule request 118's "start time" descriptor (e.g., 3:00 PM on the particular date). In other words, the schedule recommendation generation module 110 may effectively override or replace the value of a descriptor in the schedule request 118 when providing a value for that descriptor in the schedule recommendation 112. In this sense, the schedule recommendation generation module 110 may use such a descriptor value in the schedule request 118 as a suggestion. In such a case, the schedule recommendation generation module 110 may generate the "start time" descriptor (and its value) in the schedule recommendation 112 in any of a variety of ways. For example, the schedule recommendation generation module 110 may generate the "start time" descriptor (and its value) using both the schedule request 118 and the imaging examination model 106.

The schedule recommendation generation module 110 may receive the schedule request 118 from a requestor (e.g., a user 120). The user 120 may, for example, be a human who provides input to generate and provide the schedule request 118 to the schedule recommendation generation module 110. The source of the schedule request 118 may, however, not be a human. For example, the source of the schedule request 118 may be a computer program, which may provide the schedule request 118 to the schedule recommendation generation module 110 in any of a variety of ways, such as via an API. As a result, any reference herein to the user 120 should be understood to refer to any source of the schedule request 118, whether or not that source is human.

The schedule recommendation 112 may include data representing any of a variety of recommended changes to the current schedule 108. For example, the schedule recommendation 112 may include data representing a change to a descriptor in an appointment in the current schedule 108, such as a change to a value of such a descriptor (e.g., changing the duration of an imaging appointment from 30 minutes to 60 minutes). For example, the schedule recommendation 112 may include data representing a recommendation to change any one or more of the following of an imaging appointment in the current schedule 108: a start time of the imaging appointment, a duration of the imaging appointment, a scanner assigned to the imaging appointment, and an imaging protocol assigned to the imaging appointment.

The schedule recommendation generation module 110 may identify, based on the schedule request 118 and the imaging examination model 106, a recommended imaging protocol. The schedule recommendation generation module 110 may, for example, identify the recommended imaging protocol based on fewer than all of the descriptors in the schedule request 118 (e.g., based only on a patient identifier in the schedule request 118). The schedule recommendation generation module 110 may generate the schedule recommendation 112 based on the schedule request 118 and the recommended imaging protocol. The schedule recommendation 112 may, for example, include data representing a recommendation for the imaging appointment specified by the schedule recommendation 112 to use the recommended imaging protocol. The recommended imaging protocol identified by the schedule recommendation generation module 110 may, for example, be an existing imaging protocol (e.g., an imaging protocol that exists in the imaging protocol collection in the imaging provider model 122).

Alternatively, for example, identifying the recommended imaging protocol may include generating the recommended imaging protocol based on the schedule request 118 and the imaging examination model 106. In such a case, the resulting recommended imaging protocol may differ from any imaging protocol that existed in the imaging protocol collection in the imaging provider model 122 before the schedule request 118 was received by the schedule recommendation generation module 110.

As an example, identifying the recommended imaging protocol may include identifying (e.g., generating), based on an existing imaging protocol in the system 100 and the imaging examination model 106, a modified imaging protocol that differs from the existing imaging protocol. The schedule recommendation 112 may include data representing a recommendation for an imaging appointment to use the modified imaging protocol. This may be used to generate a modified imaging protocol that runs faster and therefore reduces the examination duration. As another example, if a patient is moved from one scanner to another scanner, the schedule recommendation generation module 110 may generate a modified imaging protocol that differs from the original imaging protocol that was scheduled to be performed on the patient, where the modified imaging protocol is adapted to the capabilities of the new scanner.

The schedule recommendation generation module 110 may generate the schedule recommendation 112 to recommend an imaging appointment that does not conflict with (e.g., overlap with any of the imaging appointments within) the current schedule 108.

The schedule recommendation 112 may include any of a variety of data relating to the imaging appointment recommended by the schedule recommendation 112, such as data representing any one or more of the following, in any combination: a recommended start time of the imaging appointment, a recommended duration of the imaging appointment, a recommended scanner for the imaging appointment, a recommended imaging protocol of the imaging appointment for the recommended scanner, one or a plurality of recommended alternative imaging protocols that are faster to acquire and that could be used in case the patient moves, one or more recommended hardware components to use in the imaging appointment (e.g., motion compensation system, FMRI device, special coil), a recommended preparation time for the imaging appointment, and a recommended staff member of the imaging appointment.

As described above, the imaging examination model training module 104 may train the imaging examination model 106 based on the historical imaging examination data 102. The historical imaging examination data 102 may include one or more descriptors that are labeled, such as, for example, descriptors representing start times, durations, and imaging protocols of historical imaging examinations. The schedule recommendation 112 may also include one or more descriptors that are labeled, such as the start time, duration, and/or imaging protocol of the imaging appointment that is recommended by the schedule recommendation 112. Some or all of the descriptors that are labeled in the schedule recommendation 112 may be the same as some or all of the descriptors that are labeled in the historical imaging examination data 102. For example, the historical imaging examination data 102 may include a "duration" descriptor that is labeled in the historical imaging examination data 102, and the schedule recommendation 112 may also include a "duration" descriptor that is labeled in the schedule recommendation 112.

The schedule recommendation 112 may, however, include one or more labeled descriptors that appear in the historical imaging examination data 102, but as unlabeled data, where "unlabeled data" refers to patterns that exist within the historical imaging examination data 102 with no dedicated descriptors. For example, the schedule recommendation 112 may include a labeled preparation time descriptor represented a recommended amount of preparation time to include in the imaging appointment, in addition to imaging time included in the imaging appointment, even if the historical imaging examination data 102 does not include any labeled preparation time descriptors.

The schedule recommendation generation module 110 may generate the schedule recommendation 112 in any of a variety of ways. For example, the schedule recommendation generation module 110 may use the imaging examination model 106 to generate a prediction of a duration of an appointment based on, any one or more of the current schedule 108, the schedule request 118, and/or the imaging provider model 122. The duration prediction that is generated by the schedule recommendation generation module 110 using the imaging examination model 106 may be included in the schedule recommendation 112 as a recommendation for the duration of the appointment represented by the schedule recommendation 112.

The schedule recommendation generation module 110 may, when generating an appointment duration prediction using the imaging examination model 106, take into account that different scanners can require different examination times to execute the same imaging protocol because of differences in their hardware and/or software. For example, a "diffusion MRI" protocol with a particular target image quality may be performed much more quickly on a Siemens PRISMA scanner than on a Siemens VERIO scanner. The imaging examination model 106 may include data representing such differences between such scanners, and may take such differences into account when generating a prediction of examination duration on those scanners.

As another example, the schedule recommendation generation module 110 may, when using the imaging examination model 106 to generate an examination duration prediction, take into account that different imaging protocols may require different examination durations, and hence longer appointment durations. For example:

Some imaging protocols are just quick checkups and can be performed in a short amount of time.

Some clinical indications need an imaging protocol with many more images than others to be able to do a diagnostic, and therefore require a relatively long examination duration.

Some imaging protocols involve performing more tasks than others. For example, some imaging protocols may require injecting contrast before an examination, which will increase the duration of the examination relative to a protocol that does not require such an injection.

Some protocols use imaging techniques that take more time to perform than others. For example, an "MR cardiac" protocol requires waiting between cardiac cycles in order to generate clear images, which will increase the duration of the examination relative to protocols that do not require such waiting.

The imaging examination model 106 may include data representing such differences between imaging protocols and the associated durations of such protocols, and may take such differences into account when generating a prediction of examination duration based on the imaging protocol that is used in the examination.

As another example, the schedule recommendation generation module 110 may, when using the imaging examination model 106 to generate an examination duration prediction, take into account that different patient characteristics lead (statistically, e.g., on average) to different examination durations and different pre-examination and post-examination times. For example:

Age can influence examination duration. For example, patients aged 2-5 may require a relatively long time to image because they move frequently, requiring images to be repeated.

Body mass index (BMI) can influence examination duration. For example, a breast MRI of a patient with BMI=30 may take longer than a breast MRI of a patient with BMI=15.

In-patients may require longer examination times than out-patients, for a variety of reasons.

The imaging examination model 106 may include data representing such differences between patient characteristics and the durations of examinations associated with such patient characteristics, and may take such differences into account when generating a prediction of examination duration based on the characteristics of the patient who is to be examined in the examination.

Figure 3:
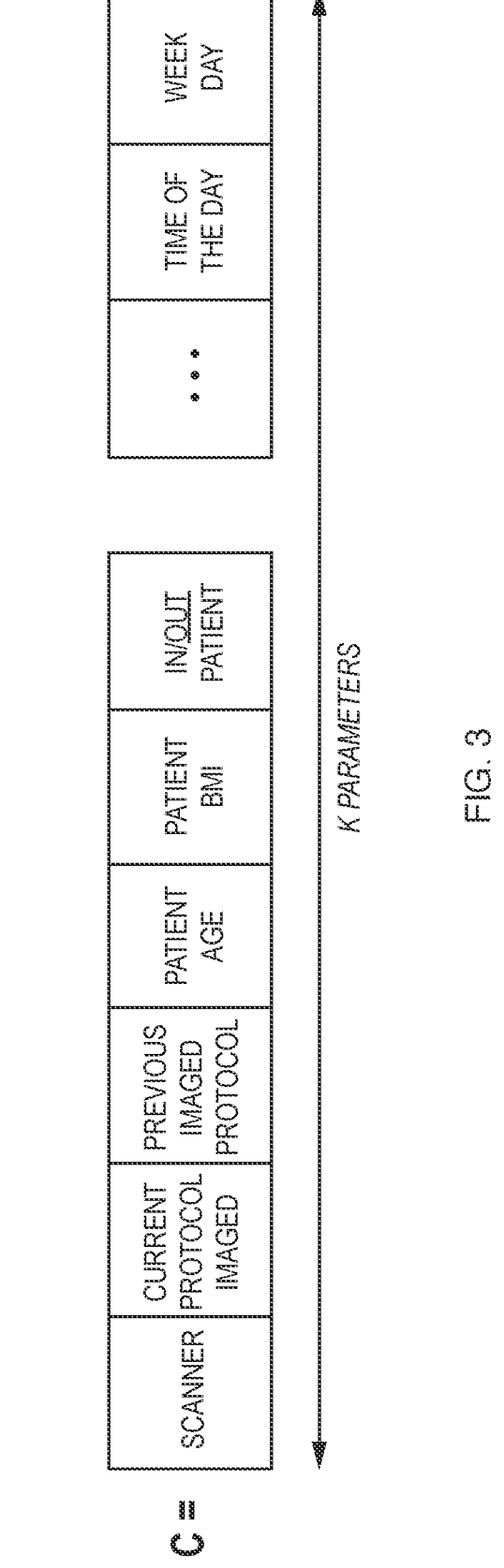
FIG. 3 is a diagram of a vector including a plurality of elements representing parameters that may impact examination duration according to one embodiment of the present invention.

Referring to FIG. 3, a diagram is shown of a vector C 300. The vector C 300 includes a plurality of elements representing descriptors (which may be confounding factors) that may impact the duration of an examination and/or an appointment. Each of the historical imaging examination data records in the historical imaging examination data 102 may, for example, correspond to a corresponding imaging examination that has been performed, and may include a vector of the kind shown in FIG. 3, where the descriptors in that vector have values taken from the corresponding imaging examination.

The imaging examination model training module 104 may apply machine learning to such vectors and duration data in the historical imaging examination data 102, thereby producing the imaging examination model 106. For example, the imaging examination model training module 104 may use such vector and duration data to identify which combination of the parameters in the vector C 300 best predict examination duration, and to build and train the imaging examination model 106. The schedule recommendation generation module 110 may use the resulting imaging examination model 106 to generate its examination duration predictions when applied to new examination descriptors (e.g., a new vector of the type C 300, containing values of parameters for an examination that is to be scheduled and which was not part of the historical imaging examination data 102 that was used to train the imaging examination model 106).

The imaging examination model training module 104 may train the imaging examination model 106 in any of a variety of ways. For example, the imaging examination model training module 104 may consider various regression models (e.g., linear regression, logit regression, SVM regression, random forest), where each such regression model produces a prediction of examination duration as a function of the vector C 300, i.e., f(C)=exam_duration. It is important to note that the above supervised learning techniques are not the only way in which the imaging examination model 106 may be trained, reinforcement learning schemes using positive rewards to predict optimal time slots could also be used in system 104.

The imaging examination model training module 104 may evaluate the ability of each of the considered regression models to accurately predict examination duration for data not used during training. For each of the considered regression models, the impact on examination duration of each confounding factor in C may be evaluated with techniques compatible with each regression model.

Embodiments of the present invention may use a granular description of each imaging protocol, such as descriptions of the kind disclosed in U.S. patent application Ser. No. 18/142,820, filed on May 3, 2023, entitled, "Identifying Medical Imaging Protocols Based on Radiology Data and Metadata," which is hereby incorporated by reference herein. Such granular protocol descriptions may go beyond those typically used in DICOM and elsewhere, which often only include a name of each imaging protocol. In contrast, embodiments of the present invention may represent imaging protocols (e.g., in the historical imaging examination data 102, schedule request 118, and/or schedule recommendation 112) with a higher degree of granularity that is precise enough so that the distribution of expected examination duration (as well as the distribution of expected number of acquisitions) for each labelled protocol is unimodal, or close to unimodal. This is, for example, not the case with a label such as, "MR Brain without contrast," because there are many different "MR Brain without contrast" imaging protocols with different expected durations, such as imaging protocols for stroke, for multiple sclerosis, for tumors, etc. Imaging protocol representations (e.g., labels) may be generated manually and/or automatically in embodiments of the present invention.

The imaging examination model may introduce the embeddings of protocols and/or examination data sets into the Vector C 300 to capture protocols with high granularity. More specifically, different examinations may include different numbers of acquisitions. As a result, different examination data sets (or protocols) may be of varying size, and therefore be "unstructured" data. The imaging examination model 106 may involve first computing an embedding of examination data sets (or protocols) to transform those into fixed-size representations, which can then be injected into the vector C 300. One way to create an embedding is to convert the examination data sets (or protocols) into graph data and to use graph learning methods, such as those described in U.S. patent application Ser. No. 18/142,820, to compute the embedding. Embeddings may be further fine-tuned by the addition of specific classifiers to better capture various features about the protocol, such as examination duration.

The schedule recommendation generation module 110 may generate the schedule recommendation 112 in any of a variety of ways. For example, the schedule recommendation generation module 110 may receive as input (e.g., from the imaging examination model 106, the current schedule 108, the schedule request 118, and/or the 122) any one or more of the following: a list of scanners available at the imaging provider, the hardware and software on each such scanner, the current schedule of appointments at the imaging provider, the imaging protocols available at the imaging provider, the list of staff available at the imaging provider, a set of soft and/or hard constraints (which may, for example, be entered manually and/or learned automatically from the historical imaging examination data 102) and the schedule request 118. The schedule recommendation generation module 110 may, for example, use a constrained resource allocation algorithm to generate the schedule recommendation 112 based on any one or more of the imaging examination model 106, the current schedule 108, the schedule request 118, and the imaging provider model 122. The constrained resource allocation algorithm may provide different solutions for different goals, e.g., to maximize scanner utilization, to maximize image quality, to best match patient availability, etc.

Although FIG. 1 only shows the single schedule recommendation 112 for ease of illustration, the system 100 and method 200 may use any of the techniques disclosed herein to generate any number of schedule recommendations, which may be the same as or differ from each other in any of a variety of ways. For example, updates to the imaging examination model 106, current schedule 108, schedule request 118, and/or imaging provider model 122 may cause the schedule recommendation generation module 110 to generate different schedule recommendations (e.g., schedule recommendations having descriptors that differ from each other) based on the updated version(s) of the imaging examination model 106, current schedule 108, schedule request 118, and/or imaging provider model 122.

For example, even if the schedule recommendation generation module 110 receives two schedule requests that are identical to each other in whole or in part (e.g., two schedule requests to perform the same imaging protocol on the same patient), the schedule recommendation generation module 110 may generate two corresponding schedule recommendations that differ from each other in any of a variety of ways, based on differences in the imaging examination model 106, the current schedule 108, and/or the imaging provider model 122 when the schedule recommendation generation module 110 processes the two different schedule requests to generate the two corresponding schedule recommendations. Such differences in the schedule recommendations may, for example, include differences in one or more descriptors representing different start times, durations, and/or imaging protocols recommended by those schedule recommendations.

As one particular example, the schedule recommendation generation module 110 may take one or more characteristics of the patient specified by the schedule request 118 when generating the schedule recommendation 112. For example, consider a case in which first patient and a second patient have different clinical conditions, and in which the first patient is more likely to move during a particular type of imaging examination (e.g., an imaging examination performed using a particular imaging protocol) than the second patient during the same type of imaging examination, due to differences in the clinical conditions of the first and second patient. As a result, the required duration of this type of imaging examination is likely to be longer for the first patient than the second patient. The schedule recommendation generation module 110 may take such differences into account when generating the schedule recommendation 112 and, for example, recommend an imaging appointment of longer duration for the first patient than for the second patient. This may be true, for example, even if the descriptors in the schedule request 118 for the first patient and the second patient are identical (e.g., even if both such schedule requests request an imaging appointment for the same clinical condition and the same imaging protocol). This is a different result than traditional scheduling techniques would produce, since such techniques would schedule imaging appointments having the same duration for both patients due to the two patients having the same clinical condition and the same imaging protocol.

Although the system 100 and method 200 illustrate the imaging examination model training module 104 as performing a single training of the imaging examination model 106 based on the historical imaging examination data 102, this is merely an example and not a limitation of the present invention. More generally, the imaging examination model training module 104 may update the training of the imaging examination model 106, such as based on updates (e.g., additions, deletions, and/or modifications) to the historical imaging examination data 102, using any of the techniques disclosed herein in connection with the training in operation 202, thereby generating one or more updated versions of the imaging examination model 106.

As another example, the imaging examination model training module 104 may update the training of the imaging examination model 106, thereby generating an update version of the imaging examination model 106, based on feedback received from one or more users (e.g., the user 120). For example, a user may provide feedback on an imaging appointment that is scheduled in the modified schedule 116 or on an imaging appointment in the modified schedule 116 that has already occurred, and the imaging examination model training module 104 may update the training of the imaging examination model 106 based on such feedback. Such feedback may, for example, be associated with the imaging appointment as a whole, or with any subset of the imaging appointment (e.g., with one or more descriptors in the imaging appointment). Such feedback may, for example, include a binary value (e.g., approve or disapprove), a ranking (e.g., on a scale, such as 1-10), or a replacement value for a descriptor in the imaging appointment (e.g., a different duration or imaging protocol).

As another example, some or all of the imaging appointments in the modified schedule 116 may be used by the imaging examination model training module 104 to update the training of the imaging examination model 106. The imaging examination model training module 104 may, for example, treat some or all of the imaging appointments in the modified schedule 116 as part of the historical imaging examination data 102 and update the training of the imaging examination model 106 using any of the techniques disclosed herein in connection with training the imaging examination model 106 based on the historical imaging examination data 102.

The system 100 may update an imaging appointment in the modified schedule 116 based on an update to the imaging appointment. In other words, when an existing appointment in the modified schedule 116 is updated to create an initial updated appointment, the schedule recommendation generation module 110 may generate a further updated appointment based on the initial updated appointment. For example, in response to an update in one descriptor in an imaging appointment in the modified schedule 116, the schedule recommendation generation module 110 may update a different descriptor in the imaging appointment. As a particular example of this, in response to updating the imaging protocol descriptor in an existing appointment in the modified schedule 116 to create an initial updated appointment, the schedule recommendation generation module 110 may update the duration descriptor in the initial updated appointment to reflect the different amount of time required to perform the new imaging protocol, thereby generating a further updated appointment. As a particular example of this, in response to updating the scanner descriptor in an existing appointment in the modified schedule 116 to create an initial updated appointment, the schedule recommendation generation module 110 may update the imaging protocol descriptor in the initial updated appointment to reflect the need to use a different imaging protocol when changing to a different scanner, thereby generating a further updated appointment. The schedule recommendation generation module 110 may perform such updates to the initial update appointment in the modified schedule 116 in any of a variety of ways, such as by applying any of the techniques disclosed herein in connection with operations 204-206 to the initial updated appointment.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more computers, computer processors, and/or other elements of a computer system. Such features are either impossible or impractical to implement mentally and/or manually. For example, embodiments of the present invention may apply machine learning to learn a model of examination duration based on the variety of data disclosed herein. Such functions are inherently rooted in computer technology and cannot be performed mentally or manually.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

Any step or act disclosed herein as being performed, or capable of being performed, by a computer or other machine, may be performed automatically by a computer or other machine, whether or not explicitly disclosed as such herein. A step or act that is performed automatically is performed solely by a computer or other machine, without human intervention. A step or act that is performed automatically may, for example, operate solely on inputs received from a computer or other machine, and not from a human. A step or act that is performed automatically may, for example, be initiated by a signal received from a computer or other machine, and not from a human. A step or act that is performed automatically may, for example, provide output to a computer or other machine, and not to a human.

The terms "A or B," "at least one of A or/and B," "at least one of A and B," "at least one of A or B," or "one or more of A or/and B" used in the various embodiments of the present disclosure include any and all combinations of words enumerated with it. For example, "A or B," "at least one of A and B" or "at least one of A or B" may mean: (1) including at least one A, (2) including at least one B, (3) including either A or B, or (4) including both at least one A and at least one B.

What is claimed is:

1. A method performed by at least one computer processor executing computer program instructions stored on at least one non-transitory computer-readable medium, the method comprising:

(A) training a model of imaging examinations based on data representing a plurality of historical imaging examinations, wherein the training comprises:

(i) generating at least one vector from the data representing the plurality of historical imaging examinations, each vector representing a plurality of parameters representing examination characteristics; and (ii) applying a learning algorithm to the at least one vector to produce the model of imaging examinations; and (B) generating, using an imaging provider model comprising the model of imaging examinations and a current schedule of imaging appointments, a schedule recommendation, wherein the imaging provider model provides a dynamic representation of a current state of an imaging provider, and wherein the schedule recommendation recommends a imaging appointment within the current schedule of imaging appointments.

2. The method of claim 1, wherein (B) further comprises updating the current schedule of imaging appointments based on the schedule recommendation, thereby generating a modified schedule of imaging appointments.

3. The method of claim 2, wherein updating the current schedule of imaging appointments based on the schedule recommendation comprises adding the imaging appointment to the current schedule of imaging appointments, thereby generating the modified schedule of imaging appointments.

4. The method of claim 2, wherein updating the current schedule of imaging appointments based on the schedule recommendation comprises modifying an existing imaging appointment within the current schedule of imaging appointments based on the schedule recommendation, thereby generating the modified schedule of imaging appointments.

5. The method of claim 1, further comprising:

(C) before performing (B), receiving a first request to schedule the imaging appointment, wherein the first request includes a plurality of descriptors associated with the imaging appointment; and wherein (B) further comprises generating the schedule recommendation based on the first request.

6. The method of claim 5, wherein the plurality of descriptors comprises: a descriptor representing an imaging protocol requested to be used to perform an imaging examination in the imaging appointment.

7. The method of claim 5, wherein the plurality of descriptors comprises: a descriptor representing at least one property of a patient on which an imaging examination is to be performed in the imaging appointment.

8. The method of claim 1, wherein the schedule recommendation comprises a recommendation to change at least one of a start time, a duration, a scanner, or an imaging protocol of an imaging appointment within the current schedule of imaging appointments.

9. The method of claim 1, further comprising:

(C) before performing (B), receiving a first request to schedule the imaging appointment, wherein the first request includes a plurality of descriptors associated with the imaging appointment;

wherein (B) further comprises: identifying, based on the first request and the model of imaging examinations, a recommended imaging protocol; and generating the schedule recommendation based on the first request and the recommended imaging protocol; wherein the schedule recommendation comprises a recommendation for the imaging appointment to use the recommended imaging protocol.

10. The method of claim 9, wherein identifying the recommended imaging protocol comprises generating the recommended imaging protocol based on the first request and the model of imaging examinations.

11. The method of claim 1, wherein (B) further comprises: modifying an existing imaging protocol to produce a modified imaging protocol that differs from the existing imaging protocol; and generating the schedule recommendation to recommend that the imaging appointment use the modified imaging protocol.

12. The method of claim 1, wherein the data representing the plurality of historical imaging examinations comprises, for each historical imaging examination in the plurality of historical imaging examinations, a duration of the historical imaging examination.

13. The method of claim 1, wherein the data representing the plurality of historical imaging examinations further comprises, for each historical imaging examination in the plurality of historical imaging examinations, an imaging protocol that was used to perform the historical imaging examination.

14. The method of claim 1, wherein the data representing the plurality of historical imaging examinations further comprises, for each historical imaging examination in the plurality of historical imaging examinations, data representing characteristics of a patient on which the historical imaging examination was performed.

15. The method of claim 1, wherein the data representing the plurality of historical imaging examinations further comprises, for each historical imaging examination in the plurality of historical imaging examinations, data representing characteristics of a scanner that was used to perform the historical imaging examination.

16. The method of claim 1, wherein the schedule recommendation includes at least one of a recommended start time of the imaging appointment, a recommended duration of the imaging appointment, or a recommended scanner of the imaging appointment.

17. The method of claim 1, wherein the schedule recommendation includes a recommended imaging protocol of the imaging appointment.

18. The method of claim 17: wherein the current schedule of imaging appointments includes a imaging appointment is associated with a first protocol descriptor describing a first imaging protocol, wherein the recommended imaging protocol represents at least one alternative protocol in relation to the first imaging protocol.

19. The method of claim 1, wherein the schedule recommendation includes a descriptor that is not labeled in the data representing the plurality of historical imaging examinations.

20. A system comprising at least one non-transitory computer-readable medium having computer program instructions stored thereon, the computer program instructions being executable by at least one computer processor to perform a method, the method comprising:

(A) training a model of imaging examinations based on data representing a plurality of historical imaging examinations, wherein the training comprises:

(i) generating at least one vector from the data representing the plurality of historical imaging examinations, each vector representing a plurality of parameters representing examination characteristics; and (ii) applying a learning algorithm to the at least one vector to produce the model of imaging examinations; and (B) generating, using an imaging provider model comprising the model of imaging examinations and a current schedule of imaging appointments, a schedule recommendation, wherein the imaging provider model provides a dynamic representation of a current state of an imaging provider, and wherein the schedule recommendation recommends a imaging appointment within the current schedule of imaging appointments.

* * * * *